United States Patent
Guin et al.

(10) Patent No.: US 9,651,491 B2
(45) Date of Patent: May 16, 2017

(54) SELECTIVE PROCESS FOR THE DETECTION OF FLUORIDE IONS

(71) Applicant: COUNCIL OF SCIENTIFIC AND INDUSTRIAL RESEARCH, New Dehli (IN)

(72) Inventors: Debanjan Guin, Maharashtra (IN); Satishchandra Balkrishna Ogale, Maharashtra (IN); Pooja Singh, Maharashtra (IN)

(73) Assignee: Council of Scientific and Industrial Research, New Delhi (IN)

( * ) Notice: Subject to any disclaimer, the term of this patent is extended or adjusted under 35 U.S.C. 154(b) by 0 days.

(21) Appl. No.: 15/121,629

(22) PCT Filed: Feb. 25, 2015

(86) PCT No.: PCT/IN2015/000106
§ 371 (c)(1),
(2) Date: Aug. 25, 2016

(87) PCT Pub. No.: WO2015/140814
PCT Pub. Date: Sep. 24, 2015

(65) Prior Publication Data
US 2016/0363536 A1    Dec. 15, 2016

(30) Foreign Application Priority Data
Feb. 25, 2014  (IN) .................... 0530/DEL/2014

(51) Int. Cl.
*G01J 1/58* (2006.01)
*G01N 21/64* (2006.01)

(52) U.S. Cl.
CPC ..... *G01N 21/6428* (2013.01); *G01N 21/6489* (2013.01); *G01N 2021/6432* (2013.01)

(58) Field of Classification Search
CPC ................................................. G01N 21/6428
See application file for complete search history.

(56) References Cited

PUBLICATIONS

PCT International Search Report for PCT/IN2015/000106, mailed Jul. 15, 2015, 4 pgs.
PCT Written Opinion on the International Searching Authority for PCT/IN2015/000106, mailed Jul. 15, 2015, 8 pgs.
Ray C Mulrooney et al: "An "off-on" sensor for flouride using luminescent CdSe/Zns quantum dots", ChemComm 2009, pp. 686-688, XP055198923, Retrieved from the Internet: URL:http://pubs.rsc.org/en/content/articlepdf/2009/cc/b817569a [retrieved on Jun. 29, 2015].
Yunsheng Xia et al: "Quantum dot based turn-on flourescent probes for anion sensing", Nanoscale, vol. 4, No. 19, 2012, pp. 5954-5959, XP55198913, ISSN: 2040-3364, DOI: 10.1039/c2nr31809a.

(Continued)

*Primary Examiner* — David Porta
*Assistant Examiner* — Hugh H Maupin
(74) *Attorney, Agent, or Firm* — Patterson Thuente Pedersen, P.A.

(57) ABSTRACT

A novel, simple, water soluble CdTe QDs based specific switch on-off-on photoluminescence (PL) based process for selective detection of fluoride ions in solutions as well as in gaseous forms.

3 Claims, 9 Drawing Sheets (56) References Cited

PUBLICATIONS

Mei Xue et al: "Hydrogen bond breakage by fluoride anions in a simple CdTe quantum dot/gold nanoparticle FRET system and its analytical application", Chemical communications (Cambridge, England), vol. 47, May 7, 2011 (May 7, 2011) pp. 4986-4988, XP55198846, England DOI: 10.1039/c0cc05389a Retrieved from the Internet: URL:http://www.ncbi.nlm.nih.gov/pubmed/21431114 [retrieved on Jun. 29, 2015].
Jianbo Liu et al: "A switchable fluorescent quantum dot probe based on aggregation/disaggregation mechanism", Chemical communications (Cambridge, England), vol. 47 Jan. 21, 2011 (Jan. 21, 2011), pp. 935-937, XP55198899, England DOI: 10.1039/c0cc03993d Retrieved from the Internet: URL:http://www.ncbi.nlm.nih.gov/pubmed/21076762 [retrieved on Jun. 29, 2015].
Hong Jinqing et al: "Quantum dot-Eu3+ conjugate as a luminescence turn-on sensor for ultrasensitive detection of nucleoside triphosphates", Talanta, vol. 99, Aug. 1, 2012 (Aug. 1, 2012), pp. 939-943, XP028936774, ISSN: 0039-9140, DOI: 10.1016/J.TALANTA.2012.07.062.

SELECTIVE PROCESS FOR THE DETECTION OF FLUORIDE IONS

RELATED APPLICATIONS

The present application is a National Phase entry of PCT Application No. PCT/IN2015/000106, filed Feb. 25, 2015, which claims priority from IN Patent Application No. 0530/DEL/2014, filed Feb. 25, 2014, each of which is hereby fully incorporated herein by reference.

FIELD OF THE INVENTION

The present invention relates to a novel, simple, rapid (less than 10 sec), sensitive, and specific photoluminescence [PL] on-off-on (over 90% PL quenching with addition of Eu3+ ions and then over 85% PL recovery with addition of F− ions into CdTe-MPA-Eu3+ solution) assay for the detection of fluoride ions.

BACKGROUND OF INVENTION

Colloidal semiconductor quantum dots (QDs), with the radii around several nanometers, have unique photoluminescence (PL) properties due to the quantum confinement effect of the charge carriers. QDs possess higher PL quantum efficiency, tunable luminescence depending only on their size, wide continuous absorption, narrower PL band, and higher photo stability over conventional organic fluorescent dyes. Since hydrophilic QDs were first used as fluorescence probes in cellular labeling in 1998, QDs have attracted widespread attention from the fields of biology and medicine and achieved remarkable progress in biomedical applications. Along with biomedical applications, sensing schemes based on fluorescence resonant energy transfer (FRET) or photo induced electron transfer (PET) have also been developed for detecting small molecules, and for tracing bio recognition events or bio catalytic transformations. Chen and Rosenzweig reported the first practical use of CdS QDs as chemical sensors to determine Zn (II) and Cu (II) ions in aqueous media. Recently, great attention has been paid to the applications of QDs as metal ion probes because of the environmental and biological importance of metal ions. Depending on the nature of QDs as well as surface coatings, a number of QDs-based probes were developed for transition metal ions, including $Hg^{2+}$, $Cu^{2+}$, $Ag^+$, and $Pb^{2+}$. Nevertheless, very little attention has been paid to the fluorescence behavior of QDs in the presence of various chemical species mainly anionic pollutants.

An article titled, "Eu3+-doped water-soluble CdTe quantum dots prepared by one-pot approach" by B. R. C. Vale, J. C. L. Souza, J. L. Ferrari, M. A. Schiavon reports the Eu3+-doped MPA-CdTe, wherein a red-shift was observed for both absorption and emission spectra, with an increase of PL intensity.

An article titled, "Detection of Hg2+ and F− ions by using fluorescence switching of quantum dots in an Au-cluster-CdTe QD nanocomposite" by Paramanik B, Bhattacharyya S, Patra A in Chemistry, 2013 May 3; 19(19):5980-7 reports a single probe of an Au nanocluster-CdTe quantum dots nanocomposite has been developed by using tripeptide-capped CdTe quantum dots (QD) and bovine serum albumin (BSA) protein-conjugated Au25 nanocluster (NC) for detection of both Hg(2+) ion and F(−) ion. A significant signal off (74% PL quenching at 553 nm) phenomenon of this nanocomposite is observed in presence of 6.56×10(−7) M Hg(2+) ion, due to salt-induced aggregation. However, a dramatic PL enhancement (128%) of the Au-NC-CdTe QD nanocomposite is observed in presence of 8.47×10(−7) M F(−) anion. The calculated limit of detections (LOD) of Hg (2+) ion concentration and F(−) ion concentration are found to be 9 and 117 nM, respectively.

An article titled, "Highly fluorescent fluoride-responsive hydrogels embedded with CdTe quantum dots" by Juan Zhou, Haibing Li in ACS Applied Materials & Interfaces January 2012; 4(2):721-4 reports functionalized CdTe quantum dots (QDs) synthesized via ion exchange that demonstrated a selective response toward fluoride in aqueous solutions based on a rapid sol-gel transition that was visible to the naked eye. The fluoride-induced hydrogel exhibited excellent fluorescent performance because of the incorporation of QDs. As a result, this highly fluorescent fluoride-induced hydrogel may pave a new way to sense fluoride using a visible sol-gel transition.

An article titled, "A new nanoprobe based on FRET between functional quantum dots and gold nanoparticles for fluoride anion and its applications for biological imaging" by Xue M, Wang X, Duan L, Gao W, Ji L, Tang B. in Biosens Bioelectron, 2012 June-July; 36 (1):168-73 reports a new nanoprobe that was designed for the fluorescence imaging of fluoride anion (F(−)) in living cells with high sensitivity and selectivity. The design is based on the fluorescence resonance energy transfer (FRET) between CdTe quantum dots (CdTe QDs) and gold nanoparticles (AuNPs) through the formation of cyclic esters between phenylborinic acid and diol.

An article titled, "Preparation of europium-quantum dots and europium-fluorescein composite nanoparticles available for ratiometric luminescent detection of metal ions" by Dong H, Liu Y, Wang D, Zhang W, Ye Z, Wang G, Yuan J. Nanotechnology, 2010 Oct. 1; 21(39):395504 reports two types of europium-containing dual-luminophore silica nanoparticles, silica-encapsulated CdTe quantum dots (CdTe QDs)-BHHCT-Eu(3+) complex nanoparticles and BHHCT-Eu(3+) surface-bound silica-encapsulated fluorescein isothiocyanate (FITC) nanoparticles (BHHCT: 4,4'-bis(1",1",1", 2",2",3",3"-heptafluoro-4",6"-hexanedion-6"-yl) chlorosulfo-o-terphenyl), were successfully prepared using a water-in-oil (W/O) reverse microemulsion method. The results of transmission electron microscopy and luminescence spectroscopy characterizations indicate that the two types of nanoparticles are all monodisperse, spherical and uniform in size (approximately 50 nm in diameter), and have well-resolved and stable dual luminescence emission properties. The CdTe QDs-BHHCT-Eu(3+) nanoparticles can be excited at 365 nm to give dual-emission peaks at 535 and 610 nm, and the FITC-BHHCT-Eu(3+) nanoparticles can be excited at 335 nm to give dual-emission peaks at 515 and 610 nm. The luminescence response investigations of the nanoparticles to different metal ions indicate that the new nanoparticles can be used as ratiometric luminescent sensing probes for the selective detection of Cu(2+) and Fe(2+) ions, respectively.

Owing to the sustained interest of selective chemosensor in environmental monitoring, the design of sensing devices based on QDs is a topic of great interest.

On the other hand, Fluoride anion has unique chemical and physiological properties, and it is also associated with nerve gases, analysis of drinking water, and the refinement of uranium. Therefore, it is necessary for environmental or biological systems to develop the effective fluorescent sensors selectively for fluoride ion.

Thus, it may be summarized that the prior art reports doping of Eu3+ in CdTe QDs but there is no doping in the present case. Inventors have introduced Eu3+ in solution which is covalently attached with carboxylic acid groups present in the surface of CdTe QDs results PL quenching of bare MPA capped CdTe QDs. Further, some inventors have used Au nanoclusters on CdTe QDS as a base system whereas the present invention uses simple CdTe QDs as a base PL sensor. Thirdly, no record is available that is applicable for HF fume detection.

Accordingly, keeping in view the drawbacks of the hitherto reported prior art, the inventors of the present invention realized that there exists a dire need to provide a sensitive, rapid (as response time is one of the important parameters for sensor application and quick response is an essential requirement to take further action) and selective process for the detection of fluoride ions in solution as well as gaseous form.

SUMMARY OF INVENTION

An object of the present invention is thus to provide a simple, rapid (as response time is one of the important parameter for sensor application and quick response is required to take further action), sensitive, and specific photoluminescence (PL) on-off-on assay for the detection of fluoride ions.

Another object of the present invention is to provide a process that is facile and does not involve tedious or cost effective procedures.

Yet another object of the present invention is to provide a process wherein the precursors used are inexpensive.

Still another object of the present invention is to provide a process which can detect fluoride ions even in HF fumes.

Yet another object of the present invention is to provide a process wherein the probe is highly selective for $F^-$, to which it is several times more sensitive as compared to all the other substances tested.

Accordingly, the present invention provides a novel, simple, water soluble CdTe QDs based switch on-off-on photoluminescence (PL) assay for speedy and selective detection of fluoride ions (F–). The steps of the process comprise adding $Eu(NO_3)_3$ to CdTe MPA QDs to get quenching of PL intensity in the sample followed by adding flouride ions to the aforesaid sample and measuring fluorescence at excitation wavelength of 380 nm and emission of 550 nm to obtain the restoration of the PL intensity.

LIST OF ABBREVIATIONS USED

PL—photoluminescence
QD—quantum dots
MPA—3-mercaptopropanoic acid
CdTe—cadmium telluride
$F^-$—fluoride ions
$SO_4^{-2}$—sulfate ions
$Cr_2O_7^{-2}$—chromate ions
$Br^-$—bromide ions
$NO_3^-$—nitrate ions
$NO_2^-$—nitrite ions
$Ni^{2+}$—Nickel ions
$Fe^{3+}$—ferric ions

BRIEF DESCRIPTION OF THE DRAWINGS

FIG. 1 depicts PL quenching of CdTe-MPA with increasing $Eu^{3+}$ concentration in Millipore water; inset corresponding calibration curve;

FIG. 2 illustrates PL recovery of CdTe-MPA-$Eu^{3+}$ with addition of $F^-$ ions in Milipore water;

FIG. 3 depicts the response time of PL recovery of CdTe-MPA-Eu QDs (switch on) with increasing concentration of $F^-$ions;

FIG. 4 depicts the results of addition of excess $NH_4F$ into solution of CdTe-MPA QDs (blank test). Common F– ions source are sodium fluoride, ammonium fluoride;

FIG. 5 illustrates the selectivity test i.e % of PL intensity regain with addition of different anions. Bar diagram for the selectivity test results obtained with the addition of different anions, cations and amino acids into CdTe-MPA-Eu system: a) CdTe-MPA, b) CdTe-MPA-$Eu^{3+}$, c) CdTe-MPA-Eu—$F^-$, d) CdTe-MPA-Eu-thiosulfate, e) CdTe-MPA-Eu—Cl, CdTe-MPA-Eu-potassium per sulfate, g) CdTe-MPA-Eu—$SO_4^{2-}$, h) CdTe-MPA-Eu—$Br^-$, i) CdTe-MPA-Eu—$NO_3^-$, j) CdTe-MPA-Eu—$Cr_2O_7^{2-}$, k) CdTe-MPA-Eu-sodium tri phosphate, 1) CdTe-MPA-Eu—$NO_2^-$, m) CdTe-MPA-Eu—$Ni^{2+}$, n) CdTe-MPA-Eu—$Fe^{2+}$, o) CdTe-MPA-Eu—$Fe^{3+}$, p) CdTe-MPA-Eu-Proline, q) CdTe-MPA-Eu-Serine, r) CdTe-MPA-Eu-Alanine, s) CdTe-MPA-Eu-Histidine;

FIG. 6 depicts Selectivity tests with different salts [Left to Right]: CdTe-MPA, CdTe-MPA-Eu, CdTe-Fluoride, CdTe-Thiosulphate, CdTe-NaCl, CdTe-K2S208, CdTe-sodium sulphate, CdTe-KBr, CdTe-sodium nitrite, CdTe-Ammonium dichromate, CdTe-sodium triphosphate, CdTe-Sodium nitrite;

FIG. 7 depict PL intensity increases with increasing conc of NH4F from Left (CdTe-MPA, CdTe-MPA-Eu, CdTe-MPA-Eu with increasing F– concentration;

DETAILED DESCRIPTION OF THE INVENTION

The present invention provides a novel switch on-off-on photoluminescence (PL) sensor for the specific detection of fluoride ions ($F^-$). This has been synthesized by using CdTe QDs and Europium (Eu3+) ions stabilized by the carboxylic groups of 3mercaptopropanoic acid (MPA) capped cadmium telluride (CdTe) QDs that leads to quenching of PL (switch off) of QDs.

The process is unique in giving fast response for detection of F ions (less than 10 sec). The process may be used to detect F ions in solution as well as gel form.

In view of above, the present invention provides a novel, rapid, sensitive, and specific PL on-off-on assay for the detection of fluoride ions.

Figure 9:
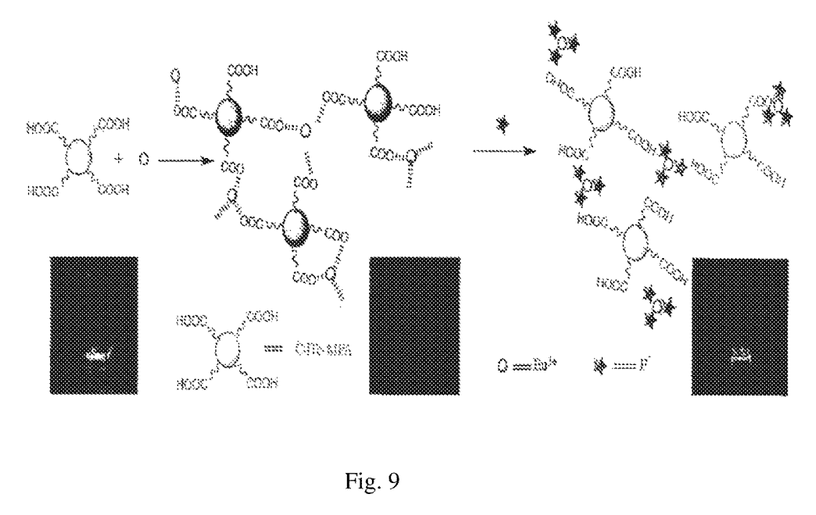
FIG. 9 is a schematic illustration of $F^-$ detection based on the competition of $F^-$ with carboxylate groups on the CdTe-MPA QDs surface for $Eu^{3+}$ ions.

The Schematic illustration of $F^-$ detection based on the competition of $F^-$ with carboxylate groups on the CdTe-MPA QDs surface for $Eu^{3+}$ ions is given in FIG. 9.

In an embodiment, the present invention provides a selective process for the detection of fluoride ions in solution or gaseous form using CdTe-MPA-Eu3+ quantum dots, wherein the steps comprise:
a) step by step addition of Eu $(NO_3)_3$ to 2 mL solution (2 mg/mL) CdTe MPA QDs to get quenching of PL intensity in the sample at excitation wavelength of 380 nm and emission of 550 nm wherein over 90% of the PL of CdTe-MPA is quenched by the addition of 56 μM $Eu^{3+}$ ions;

b) adding 1.4 mM to 79 mM fluoride ions to the sample of step (a) and measuring the fluorescence at excitation wavelength of 380 nm and emission of 550 nm obtained due to the restoration of the PL intensity, wherein a linear relationship between the enhanced PL intensity of the CdTe-MPA-Eu$^{+3}$ and the concentration of fluoride ions is observed.

In another embodiment of the present invention, the HF fumes sensing can act as a potential replacement to the commercially used but expensive fluoride sensing diagnostic kits.

In yet another embodiment, the present invention provides a process with high selectivity and sensitivity of PL quenching with F$^-$ ions which will promote the use of CdTe-MPA-Eu$^{3+}$ as a versatile probe in the fields of analytical determination, water treatment and biotechnology in the future.

In still another embodiment of the present invention, the CdTe-MPA-Eu3+ system (in solution and also in gel form) is applicable for the selective detection of HF fumes also.

EXAMPLES

The following examples are given by way of illustration and therefore should not be construed to limit the scope of the present invention.

Example 1

Quenching and Restoration of PL Intensity:
a. Mechanism:

The PL intensity of CdTe-MPA QDs (switch on) quenched instantly with the addition of Eu(NO$_3$)$_3$ addition as initially, Eu$^{3+}$ ions coordinate to the free carboxylate groups of MPA on the surface of the CdTe QDs. This results in a bridge for the induction of CdTe QD aggregation as shown in Scheme 1. As a consequence, the PL of CdTe QDs is quenched (switch off) through energy-transfer or electron-transfer processes. Then, nonfluorescent CdTe-MPA-Eu$^{3+}$ QD aggregates gets dissociated after the introduction of F$^-$ because Eu$^{3+}$ ions display a higher affinity for small fluoride anion than for the carboxylate groups existing on the CdTe-MPA QD surface. In this case, the subsequent redistribution of QDs results in the restoration of PL (switch on).

b. Process

Titration of Eu$^{3+}$ ions into the CdTe-MPA solution results in PL quenching, which can be ascribed to the aggregation of CdTe-MPA as a result of the coordination of Eu$^{3+}$ to the carboxylate groups of MPA of CdTe-MPA. FIG. 1 shows the PL quenching of CdTe-MPA with increasing Eu$^{3+}$ concentration in Millipore water and its corresponding calibration curve. It is observed that the PL intensity at 560 nm decreases as the concentration of Eu$^{3+}$ ions increases. Over 90% of the PL of CdTe-MPA (2 mg/mL) is quenched by the addition of 56 μM Eu$^{3+}$ ions. To reveal the response time of PL quenching, time-resolved PL spectra was carried out and result shows the reaction time for PL quenching is less than 30 sec.

The addition of F$^-$ to CdTe-MPA-Eu$^{3+}$ nanocomposite aggregates leads to the recovery of PL emission due to the desorption of Eu$^{3+}$ from the surface of the CdTe-MPA-Eu$^{3+}$ as a result of the competition for Eu$^{3+}$ ions between the F$^-$ and those from the carboxylate groups on the MPA on the CdTe QDs surface (FIG. 2). A linear relationship between the enhanced PL intensity of CdTe-MPA-Eu$^{3+}$ and the concentration of F$^-$ added is observed in FIG. 3. The response time to recover PL is less that 10 sec.

Example 2

Quenching and Restoration of PL Intensity in HF Fumes

Figure 8:
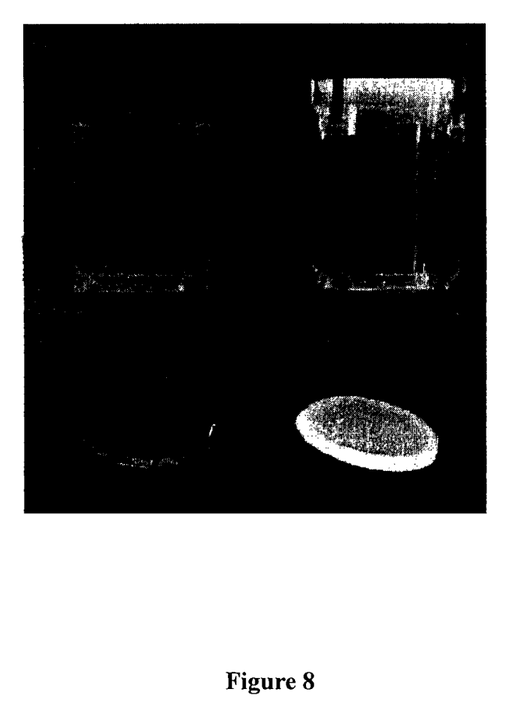
FIG. 8 Pictures of CdTe-MPA-$Eu^{3+}$ in PBS buffer pH-7.2 and agarose gels before (left) and after (right) contact with HF fumes in UV light.

To determine possible selective sensing of HF vapors, a PBS buffer solution and hydrogels of CdTe-MPA-Eu$^{3+}$ (Switch off) were kept under vapors of different acids and bases (HCl, HF, NHO$_3$, NH$_3$, NH$_2$NH$_2$). The PL recovery was observed only in the case of HF vapors whereas all other cases no change was observed in PL. The PL recovery phenomena are shown in FIG. 8.

Example 3

Hydrogels of CdTe-MPA-Eu$^{3+}$ 1 ml CdTe-MPA-Eu3+ solution was mixed with 10 mg agarose powder and heated to 45° C. to get a clear homogeneous solution. The solution was then cooled to room temperature to obtain the CdTe-MPA QD immobilized agarose hydrogel.

Example 4

Selectivity of PL Sensor for Fluoride Ions

Considering the promise of the CdTe-MPA-Eu$^{3+}$ nanocomposite as a PL sensor system for application in biological and environmental fields, the selectivity of the photoluminescent sensor for F$^-$ was evaluated. This was achieved by monitoring the PL responses of the CdTe-MPA-Eu$^{3+}$ nanocomposite complex upon addition of F$^-$ and some coexisting substances, including anions such as thiosulphate, chloride, S2O8$^{2-}$, phosphate, bromide, sulphate, nitrite, nitrate, iodide, dichromate and cations such as nickel, iron (II), iron (III) and amino acids such as proline (Pro), serine (Ser), alanine (Ala), and histidine (His), all of which were kept at a concentration fifty times higher than that of F$^-$. As shown in FIG. 5 and Scheme 1, F$^-$ can significantly restore the PL intensity of the CdTe-MPA-Eu$^{3+}$ nanocomposite in the presence of all potential competitors tested. In contrast, no clear enhancement is observed with any other ions or amino acids. The results demonstrate that this on-off-on PL probe is highly selective for F$^-$, to which it is several times more sensitive as compared to all the other substances tested. This high specificity could be attributed to the specific and robust affinity between Eu$^{3+}$ ions and F$^-$, and the off-on nature of the assay presented.

ADVANTAGES OF THE INVENTION

The process is facile and does not involve tedious or cost effective procedures.

The precursors used are inexpensive.

Sensor disclosed herein can detect fluoride ions even in HF fumes.

The probe is highly selective for F$^-$, to which it is several times more sensitive as compared to all the other substances tested.

The new NP sensor provides remarkable performance and hence offers a practical alternative to the commercially available fluoride sensors.

The invention claimed is:

1. A selective process for the detection of fluoride ions in solution or gaseous form using CdTe-MPA-Eu$^{3+}$ quantum dots, wherein the steps comprise:

a) step by step addition of Eu $(NO_3)_3$ to 2 mL solution (2 mg/mL) CdTe MPA QDs to get quenching of photoluminescence (PL) intensity in the sample at excitation wavelength of 380 nm and emission of 550 nm wherein over 90% of the PL of CdTe-MPA is quenched by the addition of 56 µM $Eu^{3+}$ ions;

b) adding 1.4 mM to 79 mM fluoride ions to the sample of step (a) and measuring the fluorescence at excitation wavelength of 380 nm and emission of 550 nm obtained due to the restoration of the PL intensity, wherein a linear relationship between the enhanced PL intensity of the CdTe-MPA-$Eu^{+3}$ and the concentration of fluoride ions is observed.

2. A process as claimed in claim 1, wherein the recovery of PL intensity with addition of $F^-$ ions is selective, sensitive and rapid (less than 10 seconds required for PL recovery) which promotes the use of CdTe-MPA-$Eu^{3+}$ as a versatile probe in the fields of analytical determination, water treatment and biotechnology.

3. A process as claimed in claim 1, wherein the fluoride ion source is selected from HF.

* * * * *